United States Patent [19]

Walt

[11] Patent Number: 5,143,853
[45] Date of Patent: * Sep. 1, 1992

[54] ABSORBANCE MODULATED FLUORESCENCE DETECTION METHODS AND SENSORS

[75] Inventor: David R. Walt, Lexington, Mass.

[73] Assignee: Trustees of Tufts College, Medford, Mass.

[*] Notice: The portion of the term of this patent subsequent to Apr. 18, 2006 has been disclaimed.

[21] Appl. No.: 305,176

[22] Filed: Feb. 2, 1989

Related U.S. Application Data

[63] Continuation of Ser. No. 878,128, Jun. 25, 1986, Pat. No. 4,822,746.

[51] Int. Cl.$^5$ .................. G01N 33/53; G01N 33/536; G01N 21/00
[52] U.S. Cl. .................. 436/501; 436/518; 436/528; 436/536; 436/546; 436/172; 436/800; 436/805; 436/56; 436/164; 436/165; 435/808
[58] Field of Search .............. 435/808; 436/507, 518, 436/528, 536, 546, 172, 800, 805, 56, 164, 165; 422/55, 59, 901; 358/901; 350/96.1, 96.2, 96.3, 96.17

[56] References Cited

U.S. PATENT DOCUMENTS

| | | | |
|---|---|---|---|
| 4,174,384 | 11/1979 | Ullman et al. | 436/800 |
| 4,495,293 | 1/1985 | Shaffar | 436/501 |
| 4,929,561 | 5/1990 | Hirshfeld | 436/74 |

*Primary Examiner*—Esther L. Kepplinger
*Assistant Examiner*—Toni R. Scheiner
*Attorney, Agent, or Firm*—David Prashker

[57] ABSTRACT

A variety of methods and apparatus for the detection of an analyte of interest in a fluid sample is provided which relies upon the interaction of a fluorophore and a chromophoric light absorbing compound for qualitative and quantitative results. The methods preferably employ fiber optic sensors in combination with fluorophores and/or proto-absorber substances in mobile and immobilized modes of use. The methods and apparatus rely upon the ability of the light absorbing compositions to absorb energy which is transferred either radiatively or non-radiatively by the fluorophore when in an excited state.

14 Claims, 5 Drawing Sheets

ABSORBANCE MODULATED FLUORESCENCE DETECTION METHODS AND SENSORS

This is a continuation of Application Ser. No. 878,128, filed on Jun. 25, 1986 now U.S. Pat. No. 4,822,746.

FIELD OF THE INVENTION

The present invention is generally concerned with fluorescence detection methods and apparatus and is directed to methods and sensors which qualitatively and/or quantitatively detect absorbance modulated fluorescene.

BACKGROUND OF THE INVENTION

Fluorescence is a physical phenomenon based upon the ability of some molecules to absorb and emit light. With some molecules, the absorption of light (photons) at specified wavelengths is followed by the emission of light from the molecule of a longer wavelength and at a lower energy state. Such emissions are called fluorescence if the emission is relatively long-lived, typically a rate near $10^{-8}$ seconds. The emission lifetime is said to be the average period of time the molecule remains in an excited energy state before it emits light of the longer wavelength. Substances which release significant amounts of fluorescent light are termed "fluorophores" and are divisible into two broad classes: intrinsic fluorescent substances and extrinsic fluorescent substances. Intrinsic fluorophores comprise the naturally occuring biological molecules whose demonstrated ability to absorb exciting light and emit light of longer wavelengths is directly based on their internal structure and chemical formulation. Typical examples include proteins and polypeptides containing tryptophan, tyrosine and phenylalamine. In addition, enzymatic cofactors such as NADH, FMN, FAD, and riboflavin are highly fluorescent. Extrinsic fluorophores, for the most part, do not occur in nature and have been developed for use as dyes to label proteins, immunoglobulins, lipids, and nucleic acids. This broad class includes fluorescein, rhodamine, and their isocyanates and isothiocyanate derivatives; dansyl chloride; naphthylamine sulfonic acids such as 1-anilino-8-naphthalene sulfonic acid ("ANS") and 2-p-toluidinylnaphthalene-6-sulfonic acid ("TNS") and their derivatives; acridine orange; proflavin; ethidium bromide; quinacrine chloride; and the like.

Figure 1:
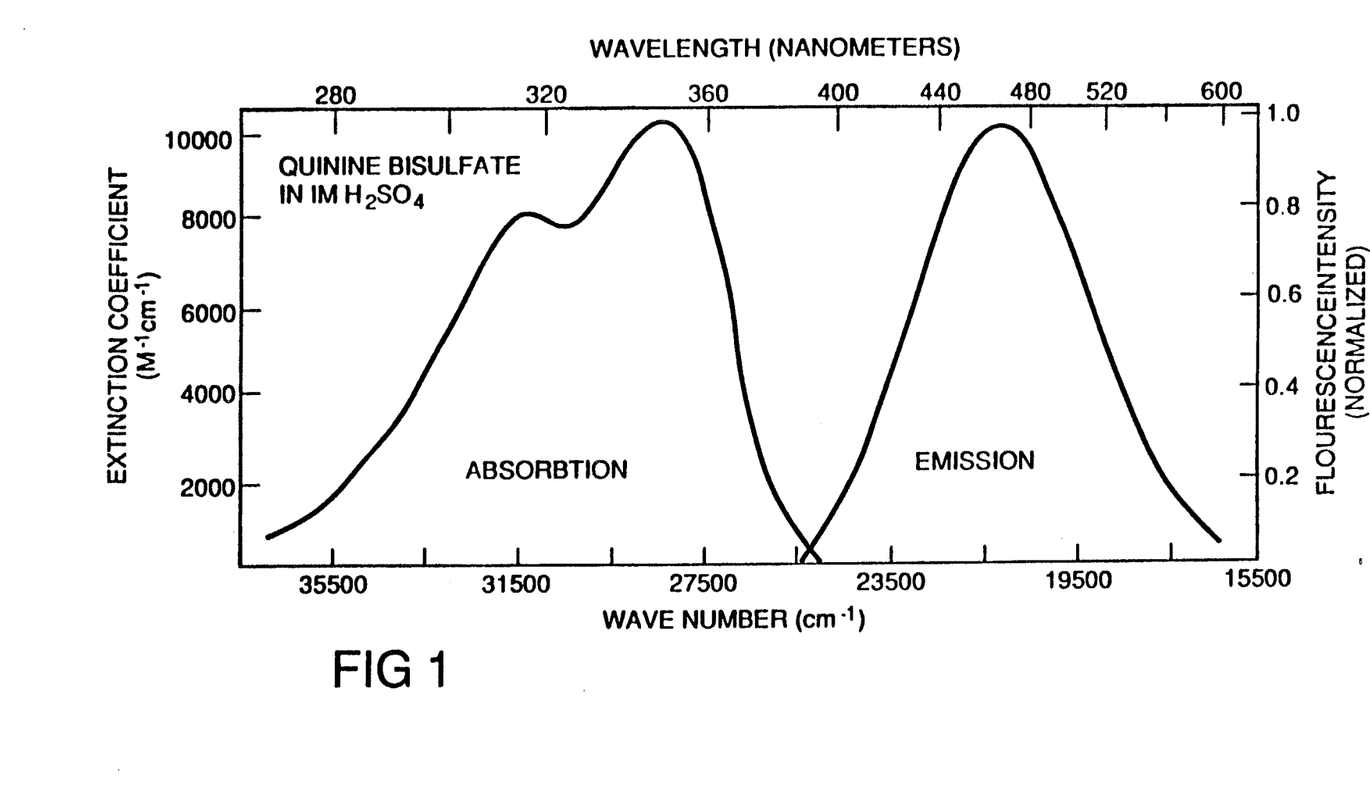
FIG. 1 is a graphic illustration of the absorption and fluorescent emission spectra of quinine bisulfate.

Substances able to fluoresce share and display a number of common characteristics: fluorophores display the ability to absorb light at one wavelength or frequency, reach an excited energy state, and subsequently emit light at another light frequency and energy level. The absorption and fluorescence emission spectra are individual for each fluorophore and are often graphically represented as two separate curves which are slightly overlapping. The absorption spectrum for quinine bisulfate is depicted in FIG. 1 and is representative of fluorescent substances in general. All fluorophores demonstrate the Stokes' Shift—that is, the emitted light is always at a longer wavelength (and at a lower energy level) relative to the wavelength (and the energy level) of the exciting light absorbed by the substance. Moreover, the same fluorescence emission spectrum is generally observed irrespective of the wavelength of the exciting light; accordingly, the wavelength and energy of the exciting light may be varied within limits, but the light emitted by the fluorophore will provide the same emission spectrum. Finally, fluorescence may be measured as the quantum yield of light emitted; the fluorescence quantum yield is the ratio of the number of photons emitted in comparison to the number of photons absorbed. The quantum yield of photons and the timed duration over which that quantity of emitted light is detectable may be modified by a variety of factors. For more detailed information regarding each of these characteristics the following references are recommended: Lakowicz, J. R., *Principles of Fluorescence Spectroscopy*, Plenum Press, New York, 1983; Freifelder, D., *Physical Biochemistry*, Second Edition, W. H. Freeman and Company, New York, 1982.

Analytical methods utilizing extrinsic fluorophores have had to conform to several specific requirements in order to be useful: (1) the fluorophore must be capable of being tightly bound at a specific location or to a unique chemical entity; (2) its fluorescence must be sensitive to those changes in the environmental test conditions or system indicative of chemical change; and (3) the fluorophore should not itself affect the features or properties of the molecule being investigated. In practical effect, this has required the investigator to adapt one of two functional approaches: to utilize fluorophores which themselves demonstrate the capacity to specifically bind to a preselected ligand or analyte of interest; or to chemically combine a non-specific fluorophore with another composition which has the requisite specific binding capacity to form a conjugate molecule, the binding specificity of the conjugate being provided by the other compound while the light emitting capability is provided by the fluorophore. Each approach is exemplified by the presently known qualitative and quantitative assay methods now well established in the art.

For example, the fusion of a fluorophore with a specific antibody has been employed in two applications. First, by the use of such fluorescent labelled specific antibody for the study of specific macromolecules or cells in tissue sections. Specific cells or tissues are combined with a conjugate comprising the fluorophore and the antibody which is then applied over a section of prepared tissue; the attachment of the fluorescent labelled antibody identifies the existence of a specific macromolecule within the tissue sections [Coons, A. H., *Int. Rev. Cytol.* 5:1 (1956); Coons, A. H., "Fluorescent Antibody Methods", in *General Cytochemical Methods* (Danielii, J. F., Editor) Academic Press, New York, 1958 pp. 399–422; Saint-Marie, G., *J. Histochem.* 10:250 (1962)].

A second example is the use of fluorophores in immunoassays: The fluorescent substance is again utilized as an identifying label with an immunogen whose presence in homogeneous and/or heterogeneous assays identifies the presence of a specific partner. Typically these include antibody-antigen reactions in competitive and non-competitive protocols [White, R. G., "Fluorescent Antibody Techniques", in *Immunological Methods*, (Ackroyd, J. F., Editor), Blackwell, Oxford, 1964; Nairn R. C., *Fluorescent Protein Tracing*, Livingstone, Edinborough; Goldstein, *J. Exp. Med.* 114:89 (1961); Humphrey & White, *Immunology For Students Of Medicine*, Blackwell Scientific Publications, Oxford, England, 1966, pp. 226–228].

Examples of using the fluorophore alone include the determination of the heme-binding site in hemoglobin. Hemoglobin is a complex of a small prosthetic group with the protein, apohemoglobin. The extrinsic fluor 1-anilino-8-naphthalene sulfonate (hereinafter "ANS") fluoresces when added to solutions of apohemoglobin but does not fluoresce with hemoglobin alone. The addition of heme to the apohemoglobin-ANS complex eliminates fluorescence by displacement of the ANS; accordingly, the site of attachment for the ANS and for heme must be the same. The timing as well as the location of such binding sites is identified by the fluorescence or elimination of fluorescence provided by ANS.

Similarly, the detection of a conformational change in an enzyme when the substrate becomes bound is detectable by the use of a fluorophore. 2-p-toluidylnaphthalene-6-sulfonate (hereinafter "TNS") fluoresces only if bound to another molecule; TNS fluoresces when added to the enzyme, alpha-chymotrypsin. The addition of a specific substrate for this enzyme decreases the fluorescence. Accordingly, fluorescence may be used as the means to determine both the degree of binding and the specific catalytic site for the enzyme with respect to the affinity and the location of the enzymatic reactions.

Fluorescence microscopy is another technique which has been utilized with fluorophores which have specific binding capacity and which can be transported and localized intracellularly. For example, acridine orange binds specifically to nucleic acids and fluoresces green or orange if bound to either DNA or RNA respectively. This technique has been used with eukaryotes to observe nucleic acids and chromosomes and to detect RNA in the nucleus; it has also been used with prokaryotes to localize and identify DNA.

Fluorescence and fluorescent detection methods are recognized as being completely different and distinguishable from light energy absorbance and absorption spectroscopy. When light energy waves encounter a molecule, the light energy can either be scattered or absorbed. If the light energy is absorbed, the molecule is said to be in an excited state and is termed a "chromophore". Molecules which absorb light and do not fluoresce usually convert the light energy into heat or kinetic energy unlike fluorescent molecules which re-emit the light at lower energy levels. The ability to internally convert the absorbed light energy rather than emit it as light is a primary difference between such molecules.

Molecules which absorb light energy do so at individual wavelengths and are characterized by a distinctive molar absorption (extinction) coefficient at that wavelength. Chemical analyses utilizing absorption spectroscopy using visible and ultraviolet light wavelengths in combination with the absorption (extinction) coefficient allow for the determination of concentration for specific compositions, for the assay of chemical reactions, and for the identification of individual compounds by spectral measurement. The most common use of absorbance measurement is to determine concentration which is calculated in accordance with Beer's law; accordingly, at a single absorbance wavelength, the greater the quantity of the composition which absorbs light at the single wavelength, the greater the optical density for the sample. In this way, the total quantity of light absorbed is directly correlated with the quantity of the composition in the sample.

Another application lies in those chemical reactions in which one of the reactants changes its absorbance characteristics during the course of the reaction; a common example from enzymology is the use of an enzyme to convert a substrate into a product or products, in which the substrate and/or product absorbs light at a given wavelength. Accordingly, the more of the reaction product that is formed, the greater the change in the quantity of light absorbed. The optical density over time thus provides a quantitative measure of the activity for that enzyme.

A third application is the identification of compositions by spectral measurement which relies on the existence of unique light absorbing spectra for a specific substance. Typically, the sample is tested with a range of different light wavelengths, with the absorbance at each wavelength being measured individually. The substance is identified by obtaining the spectral absorbance characteristics and comparing those specific wavelengths at which maximum absorbance of light is detected with those of known compounds.

In the traditional and established viewpoint of practitioners in this art, methods employing light absorption and techniques utilizing fluorescence are deemed to be completely independent, mutually exclusive, and entirely non-related both in principle and in practice. The underlying principles of each physical phenomenon are unique and distinguishable from the other with regard to the effects of light energy waves. Similarly, the analytical methods and apparatus developed utilizing the respective characteristics and principles of each phenomenon have led to widely divergent applications to obtain unrelated data and knowledge. Insofar as is presently known, there is no method or technique and no application which has combined and integrated the absorption and fluorescence phenomenon for any quantitative or qualitative detection.

SUMMARY OF THE INVENTION

The present invention provides a variety of methods for detecting an analyte of interest in a fluid sample, the methods being able to be performed in a variety of different modes. In the broadest mode, the method comprises the steps of: obtaining an identifiable ligand having a definable light absorption spectrum, the presence of the ligand being correlatable with the analyte of interest in the sample fluid; admixing a fluorophore with the ligand, the fluorophore being able (a) to absorb exciting light energy of a first wavelength, (b) to radiatively or non-radiatively transfer a part of the exciting energy to the ligand for absorption, (c) to emit the other part of the exciting energy as emitted light of a second wavelength; introducing exciting light of the first wavelength to the admixture sufficient to cause the fluorophore to emit light of the second wavelength, a portion of the exciting light energy being transferred to and absorbed by such ligand as is present in the admixture; and detecting the light of the second wavelength from the admixture after the partial absorption of energy by the ligand, the detected light being a measure of the analyte of interest in the sample. In the other methods provided herein, it is preferred that the ligand be combined with a specifically binding proto-absorber to form an absorption complex which is able to absorb energy transferred from the fluorophore.

In addition, a variety of apparatus for the detection of an analyte of interest in a fluid sample is provided, the presence of the analyte being correlatable with an identifiable ligand in the fluid. In its broadest aspect, such apparatus comprises: a fluorophore for admixture with an identifiable ligand in a fluid sample, the fluorophore being able to (a) absorb exciting light energy of a first wavelength, (b) to radiatively or non-radiatively transfer a part of the exciting energy to the ligand for absorption, (c) to emit the other part of the exciting energy as emitted light of a second wavelength; means for introducing exciting light of the first wavelength to the admixture sufficient to cause the fluorophore to emit light of the second wavelength, a portion of the exciting light energy being transferred to and absorbed by such ligand as is present in the admixture; and means for detecting light of the second wavelength from the admixture after the partial absorption of energy by the ligand, the detected light being a measure of the analyte of interest in the sample. Such apparatus in alternate preferred form also includes a proto-absorber molecule able to specifically combine with the identifiable ligand in the fluid to form an absorption complex which is able to absorb energy transferred from the fluorophore.

BRIEF DESCRIPTION OF THE DRAWING

The present invention may be more easily and completely understood when taken in conjunction with the accompanying drawing, in which.

DETAILED DESCRIPTION OF THE PREFERRED EMBODIMENTS

The present invention is a novel methodology performable in various modes for the qualitative and/or quantitative detection of an analyte of interest in a fluid sample using known fluorophores and conventional instrumentation for measuring fluorescence. The invention is unique in that fluorogenic substances are used in combination with light-absorbing ligands and light-absorption complexes, collectively termed "absorbers", in which the light-absorbing compositions absorb, and thus modulate, a portion of the energy transferred radiatively or non-radiatively by an excited fluorophore in a reaction admixture. In this manner, the principles of absorption spectroscopy in which ligands absorb energy without subsequent light emission are for the first time combined for analytical purposes with the principles of fluorescence spectroscopy in which fluorophores absorb light at one wavelength with subsequent emission of fluorescent light at a second longer wavelength. The interrelationship between the energy absorbing compositions having a definable light absorption spectrum with the fluorogenic substances having a definable light emitting spectrum relies upon their being partially coextensive and overlapping in their respective energy levels. The overlap of energy levels serves as the basis for the methods and apparatus comprising the present invention.

There are only four components required for practicing the methods or using the apparatus of the present invention. These are:

1. An energy absorbing composition in the form of either a light-absorbing ligand or a light-absorption complex having a definable light absorption spectrum. These compositions are generally termed "absorbers" herein to distinguish them readily in text from fluorophores. Absorbers are recognized and characterized by their ability to absorb light at a specific wavelength with internal conversion of light energy into heat or kinetic energy; their representation by an individual, an absorption coefficient which may be calculated in the conventional manner; and their absorbance of light energy in accordance with Beer's law such that absorbance measurements (spectrophotometry) may be used to determine concentration.

2. At least one fluorophore or fluorogenic substance having a definable light absorbance spectrum and a definable light emission spectrum. Such fluorophores are able to absorb exciting light (energy) of a first wavelength and subsequently to emit light (energy) of a second wavelength, commonly recognized as fluorescent light. In order to be operative within the present invention, the wavelengths of fluorescent light emitted by the fluorophore must be partially coextensive and overlapping with those light wavelengths which are absorbable by the light-absorbing ligands and/or the light absorption complexes, although the underlying reason for this requirement is an overlap of energy levels as will be described hereinafter.

3. Means for introducing exciting light (energy) to the fluorophore sufficient to cause the fluorophore to enter into an excited energy state and to transfer energy radiatively or non-radiatively to the energy absorbing ligands and absorption complexes.

4. Means for detecting the emitted light (energy) released by the fluorophore after the total energy has been absorbed in part by the light-absorbing compositions. The amount of light detected will be the result of the light emitted by the fluorophore after prior diminution or modulation of the total energy by the light-absorbing compositions in the reaction mixture. In this manner, the amount of emitted light detected will vary directly with the concentration of the light-absorbing compositions in the mixture which are, in turn, a measure of the analyte of interest in the test sample.

The principles of energy transfer between different substances are established in the literature. In general, there are two mechanisms of action for energy transfer which may occur: The first mechanism occurs when a fluorescent substance absorbs light at a first wavelength, re-emits light at a second different wavelength (fluoresces), and the emitted light of the second wavelength is absorbed by another different molecular species. The absorbance of light energy in this manner is known as radiative transfer. The second mechanism of action involves transfer of excitation energy per se. It occurs when a fluorophore absorbs exciting light of a first wavelength and is converted into an excited state. During the lifetime of this excited state, the excited fluorescent substance can transfer its energy as such to a different molecular species without use of radiating light. This type of energy transfer is termed non-radiative energy transfer. In both forms of transfer, the second, different molecular species must have energy absorption levels that overlap with the excited state energy levels of the fluorophore. The existence and degree of energy level overlap is most easily determined by examining the fluorophore's emission spectrum to ensure that it overlaps to some extent with the light absorption spectrum of the second molecular species. It will be understood, however, that with the methods comprising the present invention described herein, one or both of these mechanisms may be operating at any given time. Nevertheless, the net result in each instance will be qualitatively the same regardless of which mechanism of action is then in effect.

Since the present invention is dependent upon radiative or non-radiative energy transfer from an excited fluorescent substance to an energy absorbing composition (an absorber), it is required that the excited fluorophore and absorber have overlapping energy levels. Nevertheless, there will be many instances where the analyte of interest in a test sample or the identifiable ligand in a reaction fluid will not itself demonstrate the requisite overlap of energy absorption level (spectra) with the chosen fluorophore's light emission spectrum. In these cases, the present invention employs a proto-absorber molecule which will selectively combine with the identifiable ligand or analyte of interest to form a light-absorption complex. The formed light-absorption spectrum for the formed complex will then demonstrate the desired degree of overlap with the emission spectrum of the chosen fluorophore.

With respect to the proto-absorber molecules useful for forming light-absorption complexes with an identifiable ligand, a wide range of different compounds with varying light-absorption spectra can be employed. So long as the proto-absorber molecule employed demonstrates a selective binding capacity for the identifiable ligand under the particular test circumstances to form a light-absorption complex having the requisite degree of overlap with the excited fluorophore's emission spectrum, the true composition and/or formulation of the proto-absorber molecule is irrelevant and of no consequence. Representative examples of useful proto-absorber molecules are: brilliant yellow dye and rosolic acid for pH determinations; pararosaniline for sulfur dioxide analysis; ortho cresolphthalein for calcium evaluations; and bromo pyrogallol red for silver detection.

On this basis, therefore, it is important to note that the proto-absorber molecule or identifiable ligand may be a fluorescent material itself, having its own distinctive light absorbance and light emission spectra. In the analytical methods described herein, it is only the energy absorption (excitation) properties of such fluorescent materials which are important and of interest. While it is expected that most applications would utilize an absorber that dissipates its absorbed energy via radiationless processes, an absorber that dissipates the transferred and absorbed energy via a radiative process (fluorescence) is thus also possible and practical. The important distinction in all of these instances, however, is that it is the emission spectrum of the initially excited fluorophore which is being monitored for changes in quantity of emitted light rather than the nature and/or properties (including emission spectra) of the absorber to which energy is transferred. For purposes of the methods described herein, therefore, all such fluorescent materials, whether employed as identifiable ligands and/or proto-absorber molecules, are deemed to be within the scope of the present invention.

There are thus only three conditions imposed upon the described components comprising the present invention. First, it is preferred that the chosen fluorophore(s) be chemically neutral (non-reactive) with the analyte of interest; and preferably be chemically neutral (non-reactive) with the identifiable ligand in the fluid whose presence is correlatable with the analyte of interest; and preferably be chemically neutral (non-reactive) with the light-absorption complex, if and when formed, which is the reaction product of the identifiable ligand with a proto-absorber molecule. Second, that the formation of a light-absorption complex will be formed when desired using a proto-absorber molecule which will specifically bind with an identifiable ligand or analyte of interest in the test sample. Third, that the identifiable ligand and/or the light-absorption complex (if formed) each demonstrate an ability to absorb light at a wavelength which corresponds to the wavelength of the light emitted by the fluorophore; in other words, that the light absorbing spectrum of the absorber overlap and be partially coextensive with the light emission spectrum of the fluorophore.

INSTRUMENTATION FOR PRACTICING THE PRESENT INVENTION

Figure 2:
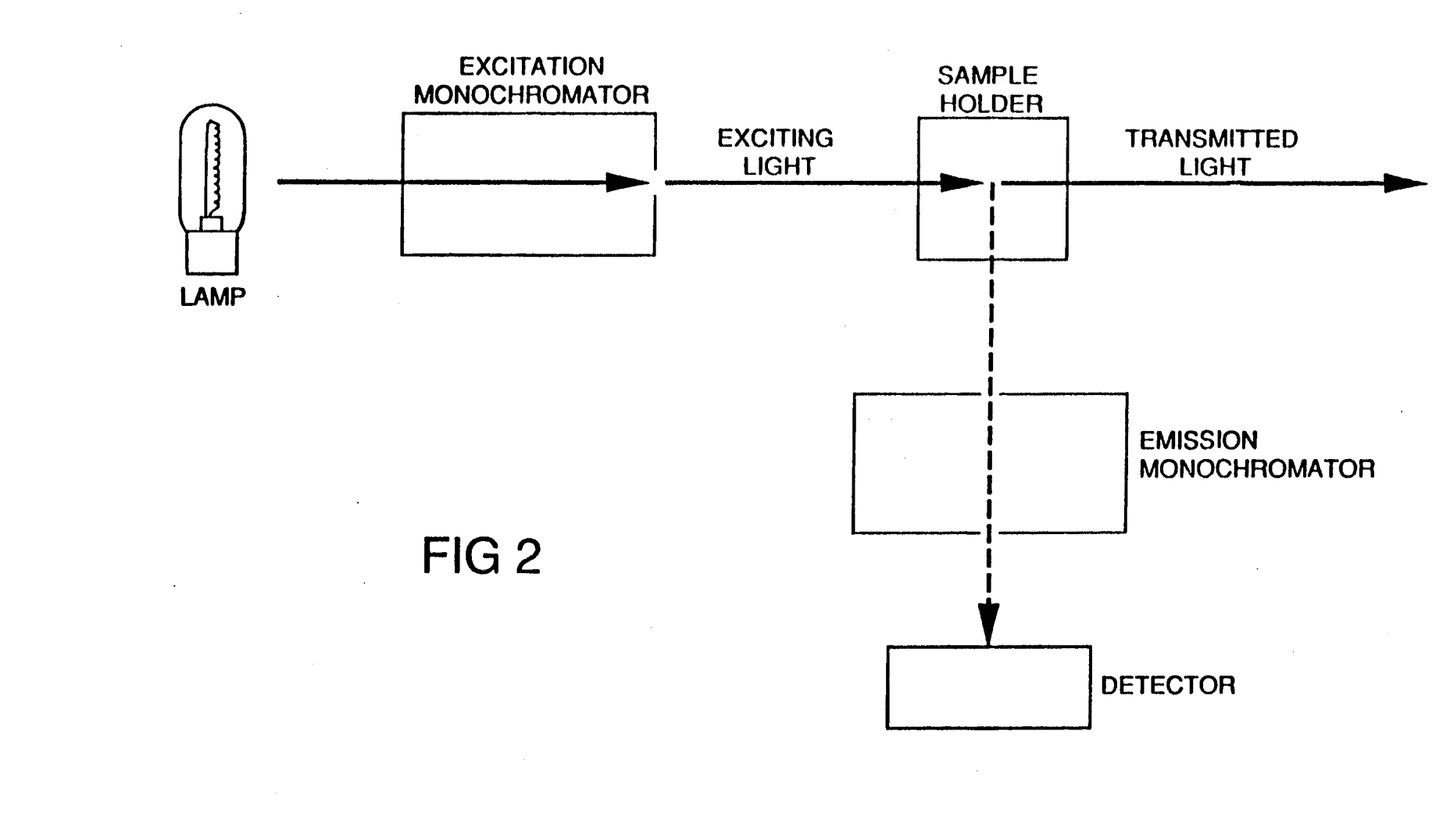
FIG. 2 illustrates the conventional instrumentation for measuring fluorescence.

A conventional, standard arrangement for measuring fluorescence is intended to be used when practicing the methods comprising the present invention. Such an arrangement is illustrated in FIG. 2. As may be seen therein, a high-intensity light beam passes through a monochromater for the selection of an excitation wavelength, a light wavelength efficiently absorbed by the fluorophore. The exciting light beam then passes through a cell containing the fluid sample. To avoid detecting the incident beam, use is made of the fact that fluorescence is emitted in all directions so that observation of the emitted fluorescent light may be made at right angles to the incident beam. The emitted fluorescence then passes through a second monochromater for wavelength analysis and finally falls on a photosensitive detector, usually a photomultiplier tube. It is expected that such instrumentation will have scanning systems and chart recorders that automatically vary the wavelength introduced as the exciting light and plot the intensity of the fluorescent light emitted as a function of wavelength of the emitted light.

Within the conventional instrumentation illustrated by FIG. 2, it is especially desirable that the means for introducing exciting light and the means for detecting the fluorescent light emitted by the reaction admixtures in the assay take the form of optic fiber strands. Such optic fibers have terminal ends comprising glass surfaces or glass beads which have been treated and which retain a porous matrix for the immobilization of fluorophores and/or for the immobilization of proto-absorber molecules. Such porous matrices and the preparation and use of fiber optic strands for the immobilization of fluorophores has been described in: Milanovich et al., "Novel Optical Fiber Techniques For Medical Application", in *Proceedings Of The SPIE 28th Annual International Technical Symposium On Optics And Electrooptics*, Volume 494, 1985; U.S. Patent Application of Hirschfeld, Ser. No. 194,684 filed Oct. 6, 1980, entitled "Remote Multi-Position Information Gathering System and Method"; pending U.S. Patent Application of David R. Walt, Ser. No. 720,750 filed Apr. 8, 1985, entitled "Method of Treating Optical Fibers and Resulting Product"; and pending U.S. Patent Application of Klainer and Walt, Ser. No. 720,745 filed Apr. 8, 1985, entitled "Amplification of Signals From Optical Fibers". The text of all these publications and pending applications are expressly incorporated by reference herein.

The methods and apparatus comprising the present invention may be usefully employed to advantage in not less than five different modes of application. Each individual mode of use represents one preferred methodology and preferably utilizes discrete, tangible fiber optic apparatus which has been modified in accordance with the requirements and restrictions for that individual mode of use. It will be expressly understood however that in each of the described modes and for each of the examples provided as an illustration of an individual mode, the use of optical fibers is merely the preferred means for introducing exciting light and is the preferred means for detecting fluorescent light emitted from the reaction admixture. Other suitable means for introducing exciting light and for detecting emitted light are conventionally known and may be employed as desired to meet the needs or convenience of the user.

In addition, it will be recognized and appreciated that each of the individually described modes of use are variations of two factors: (a) whether or not a proto-absorber molecule is utilized with an identifiable ligand to form a light-absorption complex which is used in combination with the chosen fluorophore(s); and (b) whether or not the chosen fluorophore(s) and/or proto-absorber molecule of choice (if present) is immobilized, preferably via a porous matrix. Within each described mode of use, the four essential components—the fluorophore(s), the absorber, the means for introducing exciting light, and the means for detecting emitted light—are invariably employed.

MODES UTILIZING A SINGLE FLUOROPHORE

Mode I

This mode of use utilizes freely mobile reactants in which the fluorophore is not immobilized and a proto-absorber molecule is not employed at all.

EXAMPLE 1: DETECTION OF SALICYLATE

This protocol is a modification of the published technique outlined as Procedure 530 of Sigma Diagnostics based on: Trinder, P., "Rapid Determination of Salicylate In Biological Fluids", *Biochem. J.* 57:301 (1954). The protocol calls for colorimetric measurement of a chromophoric final reaction product, the identifiable ligand, at 540 nanometers (hereinafter "nm"). The procedure utilizes the proprietary reagents prepared and sold by Sigma Diagnostics Corporation in a series of chemical reactions which remains information proprietary to that company. The Sigma kit reagents are:

0.50 ml of Blank Reagent, a proprietary "surfactant in acid" fluid preparation (true chemical formulation unknown);

0.50 ml Salicylate Standard Solution (of varied concentrations) comprising the analyte of interest in varying quantitative amounts; and 0.050 ml Color Reagent, a 1.8 molar solution of ferric nitrate in dilute acid.

The combination of these reactants in the manner specified in the kit instructions yields a chromophoric identifiable ligand, ferric salicylate, whose presence is correlatable with the analyte of interest in the test sample, salicylate.

To this final reaction product, ferric salicylate, is added the chosen fluorophore, eosin-Y (Aldrich Chemical Company) at a concentration of 1.5 milligrams per milliliter (hereinafter "mg/ml") in 0.1M citrate/monohydrogen phosphate buffer, pH 7.3 (McElwain Corporation). Using the preferred volume of 0.05 ml Color Reagent, 0.125 ml aliquot of eosin-Y solution was found to be optimal. When this analysis was reduced to the smallest convenient scale, the molar ratios of ferric ion, eosin-Y, and salicylate (using a 25 mg/dL standard) were 300:1:2. Molar ratios of reactants other than the optimal ratio are operative also to yield reproducible results.

The optic fiber preferably used in this methodology is a bare, acid-washed, 200/250 micron glass fiber. The tip of the optic fiber is immersed into the prepared admixture so as not to be close to any reflecting surface. Best results are obtained when the admixture is slightly agitated prior to exposure of the reactants to the exciting laser radiation. It was found that the wavelength of the exciting light is preferably at 488 nm for optimal sensitivity although the use of the 514 nm excitation wavelength also provides sensitivity. Using either of these wavelengths as the exciting light, a fluorescent emitted light at a wavelength of 556 nm is the maxima of the fluorophore, eosin-Y under the described assay conditions.

It will be appreciated that the reaction of the Color Reagent with the salicylate yields an identifiable ligand, ferric salicylate, whose light-absorption spectrum encompasses 556 nm. The chosen fluorophore, eosin-Y, is chemically neutral and unreactive with ferric salicylate, the final reaction product of the salicylate and the Color Reagent. In addition, it will be appreciated that the wavelength of fluorescent light emitted by the fluorophore using exciting wavelengths of light at either 488 nm or 514 nm yields an emitted light wavelength of 556 nm which is coincidental with the absorption frequency of the identifiable ligand, ferric salicylate. Accordingly, the energy contained by the fluorophore in the excited state is transferred to and absorbed in part by the ferric salicylate, the absorber, in accordance with its concentration. In this way, the amount of light emitted from the reaction admixture after partial absorption by the chromophoric reaction product ligand is a measure of the concentration of salicylate in the fluid sample. This result is exemplified by the data presented within Table 1.

TABLE 1

| Salicylate Concentration (mg/dL) | 0 | 15 | 25 | 50 | 100 |
|---|---|---|---|---|---|
| Photon Counts (thousands) Detected at 556 nm | 331 | 287 | 238 | 175 | 118 |

EXAMPLE 2: Alternative Detection of Salicylate

Identical concentrations and volumes of Blank Reagent, Salicylate Standard Solution, and Color Reagent as described in Example 1 are utilized. In this instance, however, the chosen fluorophore is amino-tetramethylrhodamine (hereinafter "TRITC-amine"). The fluorophore is prepared as an acetone solution by dissolving 0.95 milligrams of TRITC-amine (Research Organics; Cleveland, OH) in 1.0 ml of acetone. Preferably, 150 microliters of this fluorophore solution is added to the ferric salicylate, the final reaction product of the Sigma reactants and series of reactions.

Two different wavelengths of exciting light were used using the bare optic fiber previously described in Example 1. Initially, an exciting light of 488 nm was used at a power level of 3 microwatts: the fluorescent light emitted was detected at 586 nm. By empirical evaluation, it was found that the absorption maxima of TRITC-amine in acidic solution is 551 nm and that the absorption of energy by TRITC-amine at the 488 nm exciting light wavelength is not maximal. The best empirical results obtained under the test conditions using 488 nm exciting light are given in Table 2.

TABLE 2

| Salicylate Concentration (mg/dL) | 0 | 15 | 25 | 50 | 100 |
|---|---|---|---|---|---|
| Photon Counts (thousands) Detected at 586 nm | 176 | 148 | 131 | 98 | 64 |

Alternatively, if an exciting light wavelength of 514 nm is used with detection of emitted fluorescent light at the 586 nm wavelength, a much better and more consistent result is obtained. The results are given in Table 3.

TABLE 3

| Salicylate Concentration (mg/dL) | 0 | 15 | 25 | 50 | 100 |
|---|---|---|---|---|---|
| Photon Counts (thousands) Detected at 586 nm | 308 | 262 | 228 | 162 | 100 |

EXAMPLE 3: DETECTION OF BLOOD UREA NITROGEN

This assay protocol utilizes the reactants and procedural steps found described in Sigma Diagnostics Kit No. 535-Analysis of Blood Urea Nitrogen (hereinafter "BUN"). The Sigma kit instructions state that the Sigma procedure is based upon that of Crocker, C. L., *Am. J. Med. Tech.* 33:361-365 (1967). Sigma Corporation, however, does not reveal the true and exact composition and/or formulation of its BUN Acid Reagent and its BUN Color Reagent. However, based upon the Crocker reference, the formulation and concentrations are believed to be:

BUN Acid Reagent: $1.23 \times 10^{-4}$M $Fe^{+3}$ in 7.5% $H_2SO_4$;

BUN Color Reagent: diacetyl monoxime $1.7 \times 10^{-2}$M in water and 0.18% w/v thiosemicarbazide, $3.7 \times 10^{-3}$M in water.

Sigma Corporation also uses phosphoric acid in its BUN Acid Reagent (ferric chloride) but does not real the true proportions.

The novel protocol thus prepares a series of different test admixtures on the following basis. The amounts of Sigma BUN Acid Reagent and Sigma BUN Color Reagent are reduced by a factor of 2/5 while the amount of Sigma Urea Nitrogen Standard Solution is doubled. It should be noted that the Sigma standard urea solutions provide urea at a nitrogen level of 30 mg/dL (10.7 mmol/L) and at 75 mg/dL (26.75 mmol/L) respectively; both concentrations were utilized and evaluated.

To each prepared admixture of Sigma reagents was added 50 microliter increments of an ethanolic TRITC-amine solution obtained by adding 1.90 mg of TRITC-amine to 2.0 ml of ethanol to form a 0.0024M solution. The bare optic fiber was immersed in each solution in series with agitation. Laser stimulated excitation light at a wavelength of 488 nm with a power level of 3 microwatts was provided. Detection of fluorescent light emitted by the fluorophore was at the 586 nm wavelength. Photon counts (thousands) were made for test admixtures of blood urea nitrogen at 30 mg/dL and 75 mg/dL concentrations. The results are reported in Table 4.

TABLE 4

| TRITC-amine (microliters) | 50 | 100 | 150 | 200 | 250 |
|---|---|---|---|---|---|
| Photon Counts for blank solution (thousands) detected at 586 nm | 136 | 255 | 357 | 441 | 542 |
| Photon Counts for 30 mg/dL Urea Solution (thousands) detected at 586 nm | 99 | 193 | 278 | 359 | 431 |
| Photon Counts for 75 mg/dL Urea Solution (thousands) detected at 586 nm | 79 | 157 | 231 | 301 | 372 |

In addition, an evaluation was performed on a miniaturized scale in the following manner: 6.4 ml of the admixed reagents (a 3:2 ratio of Sigma BUN Acid Reagent to Sigma BUN Color Reagent) was used to dissolve 0.8 mg of TRITC-amine without any other preparation. To individual 50 ul aliquots of this prepared admixture were added varying microliter volumes of Sigma urea standard solution of concentration 30 mg/dL. Laser stimulated excitation light at wavelengths of 488 nm and 514 nm respectively were introduced to each prepared admixture. Detection of emitted fluorescent light was made at 589 nm and 590 nm respectively and recorded as photon counts (thousands) for each test sample. The results are provided in Table 5.

TABLE 5

| Final Concentration of Urea in The Admixture | Photon Counts (thousands) at 488 nm Excitation/ 589 nm Emission | Photon Counts (thousands) at 514 nm Excitation/ 590 nm Emission |
|---|---|---|
| 0.0 (blank) | 479 | 981 |
| 0.21 mM | 410 | 830 |
| 0.41 mM | 381 | 777 |
| 0.79 mM | 335 | 701 |
| 1.48 mM | 290 | 627 |

Mode 2

This mode of use employs a proto-absorber molecule in combination with the chosen fluorophore in the reaction admixture, both of which are freely mobile. The proto-absorber is an extrinsically added molecule which will specifically bind with an identifiable ligand in the fluid whose presence is correlatable with the analyte of interest in the sample. In Example 4 which follows, the assay is directed to the determination of pH in the fluid as measured by the concentration of hydrogen ion (the identifiable ligand) in the sample. The proto-absorber molecule of choice is phenol red dye (Aldrich Chemical Company) which combines specifically with the hydrogen ion in the fluid to form a chromophoric complex whose energy absorption spectrum does not overlap with the energy emission spectrum of the fluorophore, 5-amino eosin. In this instance, therefore, only the proto-absorber molecule in the unbound state has an overlapping energy absorption spectrum with the fluorophore; accordingly, the greater the concentration of hydrogen ion in the reaction mixture, the larger the quantity of chromophoric complex that is formed, and the less the quantity of unbound phenol red dye in the admixture able to absorb the energy transferred from the fluorophore, 5-amino eosin. This example is unusual in that it is the reverse of the more common situation where the formation of the complex via the interaction of the proto-absorber molecule and the identifiable ligand, creates an absorption complex in situ which only upon being formed as a complex demonstrates an energy absorption spectrum which overlaps that of the fluorophore.

In view of the foregoing, it will be recognized and expressly understood that it is merely a matter of personal choice to the user and the demands of the specific application which mechanism of action is at work with regard to the proto-absorber molecule in a reaction admixture. The investigator may thus employ: a proto-absorber molecule which in the unbound state alone overlaps the energy emission spectrum of the fluorophore but which no longer demonstrates such an overlap after binding with an identifiable ligand; or a proto-absorber molecule which in the unbound state does not overlap the energy emission spectrum of the fluorophore, but which after binding with an identifiable ligand yields an absorption complex that alone then demonstrates the requisite energy spectrum overlap. Both forms of proto-absorber molecule are deemed to be within the scope of the present invention.

EXAMPLE 4: DETERMINATION OF pH

A series of test solutions were made using the proto-absorber molecule, phenol red dye, at 1.2 mg/ml concentration; the chosen fluorophore, eosin-Y, at 1.5 mg/ml concentration; and 0.1M citrate/monohydrogen phosphate buffer adjusted to varying pH levels. 4.0 ml aliquots of pH adjusted buffer was combined with 0.4 ml of phenol red dye and 0.3 ml of eosin-Y solution. Alternative power levels of 0.3 uW and 3.0 uW were utilized at an exciting light wavelength of 488 nm. Empirically it was found that bleaching is a problem encountered when using the 3.0 uW power level; accordingly, for that power level, the quantity of phenol red dye was reduced from 0.4 ml to 0.2 ml per 4.0 ml of buffer and 0.3 ml of eosin-Y. All emitted light was detected using a bare optical fiber strand at the 546 nm wavelengths. The results are given in Table 6 below.

TABLE 6

| Power Level | pH of Sample | Photon Counts (thousands) Detected at 546 nm |
| --- | --- | --- |
| 0.3 uW | 5.73 | 45 |
| 0.3 uW | 6.55 | 44 |
| 0.3 uW | 7.26 | 39 |
| 0.3 uW | 8.12 | 32 |
| 3.0 uW | 5.73 | 46 |
| 3.0 uW | 6.55 | 46 |
| 3.0 uW | 7.26 | 44 |
| 3.0 uW | 8.12 | 39 |

Mode 3

This mode of use employs a proto-absorber molecule which will specifically combine with an identifiable ligand in the fluid to form a light-absorption complex; and a fluorophore. Both proto-absorber and fluorophore are immobilized via a porous matrix to an optic fiber strand.

EXAMPLE 5: DETERMINATION OF pH

Glass-on-glass fibers (200/250 microns) approximately one meter long are joined at one end with amp connectors. The other end of the optic fiber is stripped of clading for a length of approximately 2 centimeters. The stripped end is washed in concentrated (96%) sulfuric acid for one minute and rinsed with distilled water. A glass capillary tube is then slipped over the bare glass end for protection of the end tip and to aid in alignment of the fiber strand in the immobilization reactions. The preferred proto-absorber molecule is phenol red dye (Aldrich Chemical Company, Minneapolis, Minn.) prepared as a 0.35 mM solution by dissolving 0.125 grams of the dye in the polymerization medium described below.

The chosen fluorophore is 5-amino eosin (Molecular Probes, Junction City, Ore.) which is used in the form of N-(5-eosinyl) acrylamide prepared immediately prior to use by mixing freshly distilled tetrahydrofuran (hereinafter "THF") in 1.0 ml volumes with 0.043 grams of 5-amino eosin to yield a 0.065 mmol solution. To this preparation is added 23 microliters of acryloyl chloride to form a (0.3 mmol solution) after which the mixture is allowed to stand in the dark at room temperature for one hour.

Surface silanization of the stripped optic fiber tip was performed by submerging the clean optical fiber tip for one hour into a solution which had been prepared by: adding gamma-methacryloxypropyltrimethoxysilane (2% by volume) to water acidified to pH 3.5 with acetic acid followed by stirring for 30 minutes at room temperature. After silanization, the optic fiber tip was washed with water at pH 3.5 and then allowed to air dry.

A porous polymerized matrix immobilizing the proto-absorber molecule and the fluorophore is prepared in the following manner. A polymerization medium is made by mixing 5.0 ml of acrylamide solution, 20 ml of bis N, N' methylene-bisacrylamide solution and the phenol red dye (0.25 grams, 0.35 mmol). This reaction mixture is de-oxygenated with gaseous nitrogen and maintained in a nitrogen atmosphere within a reaction chamber. Subsequently, the THF solution of N-(5-eosinyl)acrylamide is added with stirring. Then ammonium persulfate (0.655 grams, 2.9 mmol) and TEMED, tetramethylethylene diamine, (50 microliters, 0.333 mmol) are added with stirring. The prepared optic fiber strands were immersed into this immobilization medium and the polymerization reaction allowed to proceed until a visible gel is formed. The fibers are withdrawn from the reaction medium when polymerization progresses to the extent that the medium forms into a discrete gel which does not flow when the reaction chamber is tilted. The optic fiber sensors supporting the immobilized proto-absorber and fluorophore is then soaked overnight in citrate/monohydrogen phosphate buffer, pH 7.9.

The preferred instrumentation utilizes a laser apparatus in combination with the prepared optical fiber sensor. An argon-ion laser (Spectra-Physics Model 162A-04, Mountain View, Calif.) provides a focused light beam at an exciting wavelength of 488 nm which is passed through a neutral density filter and a dichoric mirror to the coupled fiber. The detected fluorescent light returns via the same fiber and is deflected 90 degrees by the front surface of the angled dichoic mirror. This signal beam is filtered to remove radiation of wavelengths less than 520 nm, is focused, and is then passed through a slit of 1.25 nm width to a photometer (Pacific Instruments, Model 125 with a 3150 RF head, Concord, Calif.). The laser power is preferably adjusted to 3.0 microwatts. The fiber, extending from the protection of the glass capillary sheath, is placed in vertical position. Each test solution is raised for immersion of the optic fiber tip using a labjack. Emission spectra is scanned in the region ranging from 500-600 nm. All measurement of emitted light in response to variations of pH were detected at 547 nm while the fiber optic tip remained immersed in specifically buffered pH solutions. All pH values of the buffered solutions were verified by pH meter measurement prior to use. All pH response values were determined in duplicate by cycling through the entire pH range tested. The response time for the photometer was set to 3.0 seconds and intensity measurement data obtained only after a repeated lapse of three time constants for each change in solution.

It will be recognized and appreciated that by preparing the optic fiber sensors in the manner described above, a ratio of eosin dye to phenol red proto-absorber was made at a 5:1 molar ratio. Detection of the emitted light response after partial absorbance of energy by the light-absorption complex comprising the phenol red and hydrogen ion is performed by immersing the distal end of the prepared fiber optic sensor into solutions of known pH, taking care that the end of the fiber sensor does not come in close contact with a reflecting surface (such as the bottom of the glass container). Slight agitation of each test solution prior to actual measurement of emitted light is performed to ensure that residues from the previous sample are flushed from the region of the fiber sensor tip. In each instance, excitation light at 488 nm was introduced into each test solution and the detection of emitted light was made at a wavelength near the emission maximum of 546 nm. Power levels of 3.0 microwatts are preferrably used, but accurate results and sensitivity to small variations of pH are obtainable using power levels of 0.3 and 0.6 microwatts respectively. Alternatively also, the fluorescent emitted light may be detected at other wavelengths near 546-547 nm, the emission maxima for emitted fluorescent light. The results are as illustrated in FIG. 3.

Figure 3:
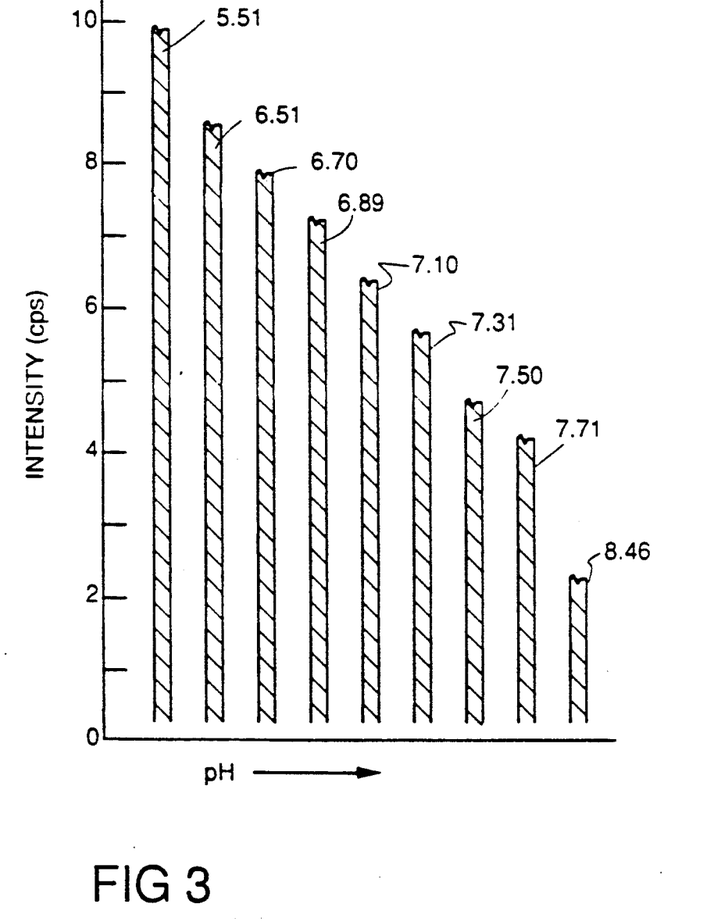
FIG. 3 is a graph illustrating the detection of emitted light as a function of changes in pH.

As seen in FIG. 3, there is a direct correlation between the intensity (cps) of emitted fluorescent light detected by the fiber sensor containing eosin and phenol red immobilized via a porous matrix. It will be recognized that by the empirical data of FIG. 3 that as the pH value increases the intensity (cps) of the emitted light after modulation by the light-absorption complex steadily decreases.

Modes 4 and 5

The remaining modes utilize the essential components in distinctly different variations of Modes 1-3 described earlier. Mode 4 employs an immobilized fluorophore on the surface of a fiber optic sensor, the immobilization of the fluorophore being provided by the previously described porous matrix gel of Example 5 while the proto-absorber molecule is utilized in mobile form for specific combination with an identifiable ligand to form a light-absorption complex. In comparison, Mode 5 utilizes a prepared optic fiber sensor containing an immobilized proto-absorber molecule within the previously described porous matrix gel while the fluorophore remains freely mobile within the fluid. It will be appreciated that each of these modes is expected to provide results comparable to any other mode of use so long as the basic conditions of analysis and essential requirements for each component are met.

It will be appreciated therefore that a wide range of different fluorophores and absorbers may be used in varying combinations and alternative mobile and immobilized forms. A preferred partial listing of fluorophores and absorbers useful in a range of different applications via each of the described modes of use is provided by Table 7.

TABLE 7

| Fluorophore | Fluorescence Emission Range ($\lambda$max) | Absorber | Energy Absorbance Range ($\lambda$max) | Application |
|---|---|---|---|---|
| Eosin | 530–580 nm (550 nm) | iron-salicylate complex | 530 nm | clinical salicylate analysis (Sigma test No. 535) |
| TRITC-amine | 570–610 nm (590 nm) | chromophoric product of urea and diacetyl monoxime | 515–540 nm | clinical BUN analysis (Sigma test No. 535) |
| Eosin | 530–580 nm | amaranth | 520 nm | measurement of amaranth released from complex with thorium and borate for sulfate analysis |
| TRITC-amine (or Eosin) | 570–610 nm | indamine dye | 590 nm | analysis of oxalate (Sigma test No. 590) |
| Quinine | 530 nm | INT formazan dye | | glucose analysis (Sigma test No. 115) |
| Eosin | 550 nm | Hopkins-Cole dye | 560 nm | globulin analysis, total (Sigma test No. 560) |
| Fluorescein W | 530 nm | calmagite-Mg complex | 520 nm | magnesium analysis (Sigma test No. 595) |
| Eosin | 530–580 nm | peptide complex with cupric ion | 540–545 nm | total protein analysis (Sigma test No. 540) |
| TRITC-amine | 590 nm | molybdate complex | 620–700 nm | inorganic phosphate (Sigma test No. 670) |
| Eosin | 560 | Azin-bis-indandion $Cu^{+2}$ complex | (blue) | cupric copper |
| Acridine yellow (excitation wavelength at 464 nm) | 500 nm | Quinone-imine dye | 500 nm | cholesterol, HDL (Sigma test No. 351) |
| Eosin (or TRITC-amine) | | calcium-cresolphthalein complex | 570 nm | calcium analysis (Sigma test No. 586) |
| Lissamine Flavine FS (excitation at 416 nm) | | $Fe(SCN)^{+2}$ | 460 nm | chloride ion analysis (Sigma test No. 460) |
| Erythroscein (excitation at 504 nm) | | azobilirubin | 560 nm | Bilirubin analysis (Sigma test No. 550) |

TABLE 7-continued

| Fluorophore | Fluorescence Emission Range (λmax) | Absorber | Energy Absorbance Range (λmax) | Application |
|---|---|---|---|---|
| Cyanosine B (excitation at 518 nm) | | triose hydrazones | 500–580 nm | aldolase analysis (Sigma test No. 750) |

MODES UTILIZING MULTIPLE FLUOROPHORES

It will be recognized and appreciated that the detailed description of the present invention in all its aspects has focused on the use of a single fluorophore and an absorber in the reaction admixture with the requisite overlap of energy levels between them. Under some circumstances, such as in a system where the exciting light energy and/or detection system are limited to narrow regions of the light spectrum, a two component system (a single fluorophore and a proto-absorber molecule or absorption complex) will not function because a sensitive absorbing species cannot be found which overlaps with the energy emission spectrum of the one useful fluorophore; or none of the available fluorophores alone can be used with the unique absorber species in a particular application due to the absence of overlapping energy spectra. In such instances, it is possible to use a plurality of different fluorophores in combination with a ligand (with or without a proto-absorber molecule) in a reactive admixture as a multi-component fluorescent system.

The method for detecting an analyte of interest in a fluid sample would thus comprise admixing the identifiable ligand in the fluid with at least two (but often more than two) different fluorophores, each of which has a unique energy absorption spectrum and an individual energy emission spectrum. Each fluorophore ($F_1$, $F_2$, $F_3$... $F_n$) is related to the other in the manner illustrated by the graphs of FIG. 4 and FIG. 5. Fluorophore $F_1$ is able to absorb exciting light energy of a first wavelength and has an energy emission spectrum which overlaps the energy absorbance spectrum of the fluorophore $F_2$. Because of this overlap, fluorophore $F_1$ is able to transfer at least a part of its absorbed energy radiatively or non-radiatively to the fluorophore $F_2$ and such transferred energy is absorbed by $F_2$. Fluorophore $F_1$ may or may not emit energy radiatively, i.e., emit fluorescent light; if $F_1$ does emit fluorescent light, the emitted light is a wavelength which fluorophore $F_2$ absorbs. If energy is transferred non-radiatively, the energy is received and absorbed by $F_2$ in the manner described earlier herein.

After absorbing the transferred energy, fluorophore $F_2$ enters into an excited state and will transfer at least a part of its absorbed energy, radiatively or non-radiatively, to another substance whose energy absorption spectrum overlaps the energy emission spectrum of fluorophore $F_2$. The substance having the requisite overlapping energy absorption spectrum can be either another fluorophore $F_3$ as illustrated in FIG. 5, or be an absorber A (an identifiable ligand or a formed absorption complex) as illustrated in FIG. 4.

Figure 4:
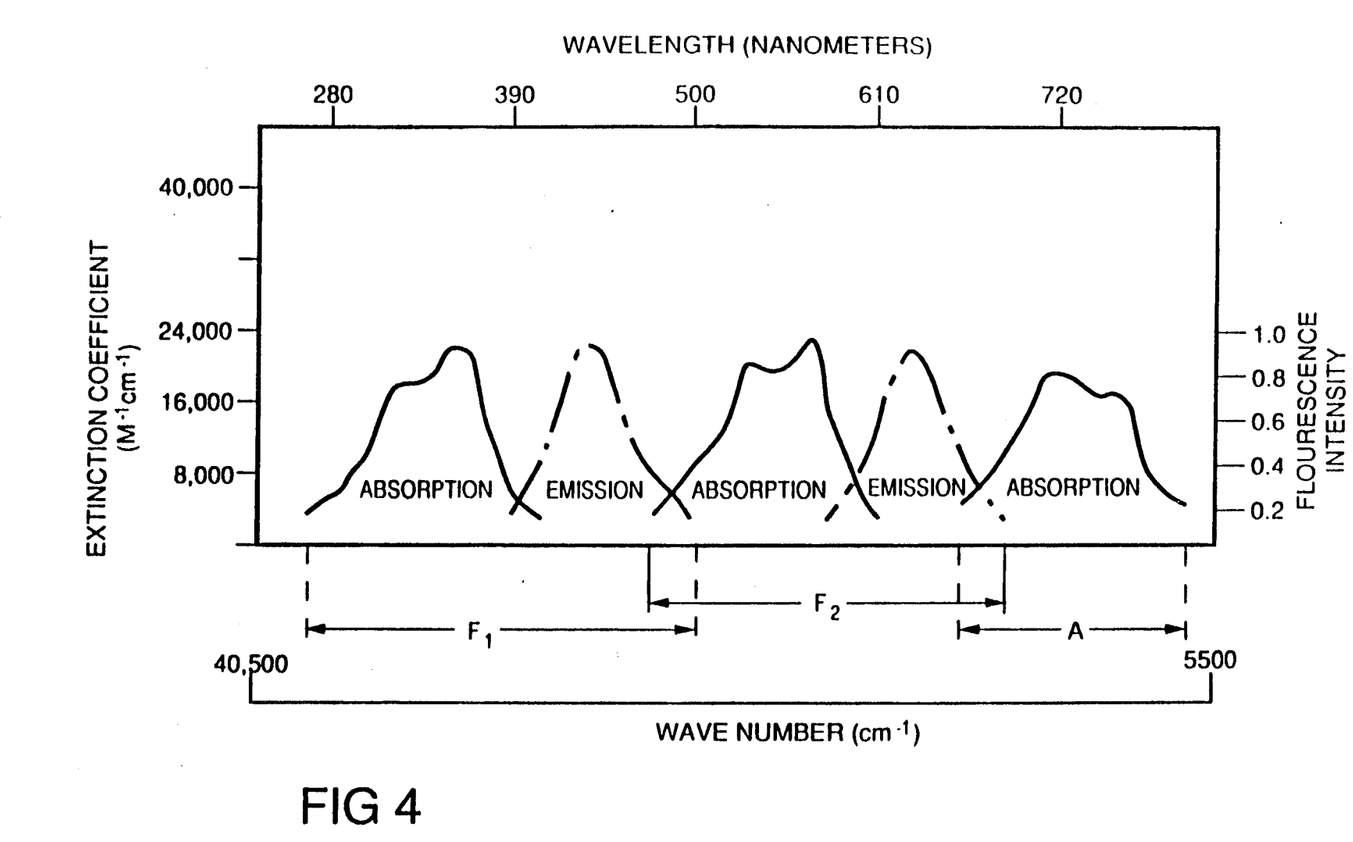
FIG. 4 is a graph illustrating the use of two different fluorophores in the invention.

FIG. 4 thus illustrates the situation where only two fluorophores $F_1$ and $F_2$ are used with an absorber A in which at least part of the absorbed energy of fluorophore $F_2$ is transferred, radiatively or non-radiatively, to the absorber A for additional absorption. Furthermore, fluorophore $F_2$ will also emit part of its absorbed energy as emitted light of a second wavelength. In this manner, when exciting light energy of the first wavelength is introduced to the reaction admixture, the fluorophore $F_1$ will absorb the exciting light energy; a part of which will be transferred to and absorbed by the absorber A via the intermediate fluorophore $F_2$; and fluorophore $F_2$ will emit light energy of the second wavelength. The emitted light can be detected using conventional apparatus and is a measure of the analyte of interest in the fluid test sample.

Figure 5:
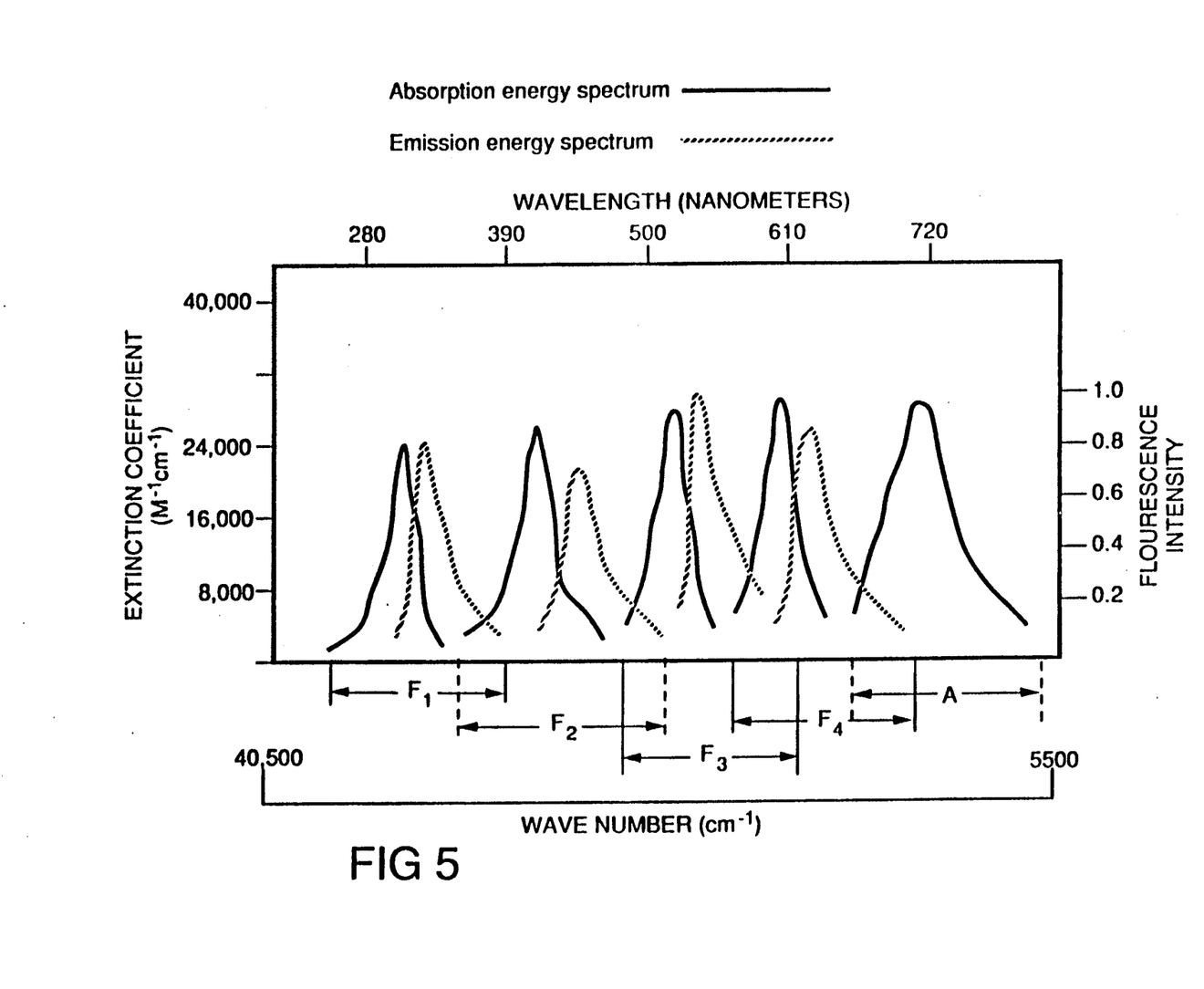
FIG. 5 is a graph illustrating the use of a plurality of different fluorophores in the invention.

FIG. 5 illustrates the situation where the spectral gap between the energy emission spectrum of fluorophore $F_1$ and the energy absorption spectrum of the absorber A is large and thus requires the use of several other fluorophores $F_3$ and $F_4$ with overlapping energy spectra as intermediates. Under these conditions, when exciting light energy of a first wavelength is introduced to the admixture, fluorophore $F_1$ absorbs the exciting energy and transfers at least a part of this absorbed energy, radiatively or non-radiatively, to another fluorophore $F_2$ for further absorption. Fluorophore $F_2$, having absorbed the transferred energy, enters into an excited state itself and transfers at least a part of the absorbed energy, radiatively or non-radiatively, to the next intermediate in series, fluorophore $F_3$; this intermediate $F_3$, in turn, enters into an excited state upon absorption of the energy transferred from $F_2$ and also transfers at least a part of its absorbed energy, radiatively or non-radiatively, to another fluorophore $F_4$. This sequence of energy transfer can be extended to include as many different fluorophores $F_n$ having overlapping energy emission and absorption spectra as are required under the circumstances to bridge the wavelength gap from the first wavelength of the exciting light energy to the energy absorption spectrum of the absorber A in sequential energy transfer series. As seen in FIG. 5, this sequence is completed by the fluorophore $F_4$ whose energy emission spectrum overlaps the energy absorption spectrum of the absorber A. Other limiting factors in determining the number of different fluorophores $F_n$ to be employed are the total quantity of exciting light energy introduced into the reaction admixture and the efficiency of the individual energy transfers among the fluorophores $F_1$... $F_n$.

It will be appreciated by the user that embodiments of the present invention illustrated by FIG. 5 allow any or all of the fluorophores $F_2$, $F_3$, $F_4$... $F_n$ to emit absorbed energy as emitted light of a second wavelength for detection, recognizing that the absorber A has modulated the emitted light of the second wavelength from any of these fluorophores by partial absorption of the energy transferred among the different fluorophores in sequential series. Thus, it is required only that at least one of the fluorophores in the admixture emit part of the absorbed energy as emitted light of the second wavelength for detection purposes; if more than one fluorophore transfers energy radiatively by emitting fluorescent light, the user may choose from among all the wavelengths of the emitted light which to utilize for detection, and in turn, for measuring the analyte of interest in the sample.

Furthermore, all that has been previously described herein regarding proto-absorber molecules, light-absorption complexes formed in-situ, and the use of mobile and immobilized components pertains to the use of multiple, different fluorophores in the reaction admixture. Similarly, the preparation and use of fiber optic sensors as the means for introducing exciting light energy and for detecting emitted light is equally appliable for embodiments employing a plurality of different overlapping energy emission and absorption spectra.

It will be appreciated that the present methods and novel apparatus for performing each mode of use described herein provide major advantages to the user not previously available in this art. These substantive advantages include: A more sensitive assay methodology due to the inherent sensitivity of fluorescence measurements compared to absorbance measurements; and the ability to reduce each assay method and each mode of use for application to very small sample volumes.

The invention is not to be restricted in form nor limited in scope except by the claims appended hereto.

What is claim is:

1. A method for detecting an analyte of interest in a fluid sample, said method comprising the steps of:

admixing the fluid sample comprising a discrete absorber ligand whose spectral properties are influenced by and correlatable with the analyte of interest in the sample with a chemically non-reactive fluorophore to form a reaction mixture, said absorber ligand having a definable light absorption spectrum, said fluorophore having a definable light absorption spectrum and a definable light emission spectrum each of which overlaps the light absorption spectrum of said absorber ligand, said fluorophore of said formed reaction mixture being able (a) to absorb exciting light energy of a first wavelength, (b) to transfer a part of said fluorophore absorbed energy to said absorber ligand of said reaction mixture for absorption, said transfer being selected from the group consisting of radiative and non-radiative energy transfers, and (c) to emit the other part of said fluorophore absorbed energy as emitted light of a second wavelength;

introducing exciting light energy of the first wavelength to said reaction mixture sufficient to cause said fluorophore to absorb said exciting light energy, wherein a portion of said fluorphore absorbed energy is transferred to and absorbed by such absorber ligand as is present in said reaction mixture, and wherein another portion of said fluorophore absorbed energy is emitted by said fluorophore as light of the second wavelength; and detecting said light of the second wavelength emitted by said fluorophore of said reaction mixture, said detected emitted light being a measure of the analyte of interest in the sample.

2. A method for detecting an analyte of interest in a fluid sample, said method comprising the steps of:

mixing the fluid sample comprising a discrete ligand whose presence is indicative of the analyte of interest in the sample with a specifically binding protoabsorber whose spectral properties are influenced by and correlatable with said ligand to form an absorption complex having a definable light absorption spectrum, at least a portion of said proto-absorber binding with such ligand as is present to form said absorption complex while the remainder of said proto-absorber remains unbound;

admixing a chemically non-reactive fluorophore with said absorption complex to form a reaction mixture, said fluorophore having a definable light absorption spectrum and a definable light emission spectrum each of which overlaps the light absorption spectrum of said absorption complex, said fluorophore of said formed ereaction mixture being able (a) to absorb exciting light energy of a first wavelength, (b) to transfer a part of said fluorophore absorbed energy to said absorber complex of said reaction mixture for absorption, said transfer being selected from the group consisting of radiative and non-radiative energy transfers, and (c) to emit the other part of said fluorophore absorbed energy as emitted light of a second wavelength;

introducing exciting light energy of the first wavelength to said reaction mixture sufficient to cause said fluorophore to absorb said exciting light energy, wherein a portion of said fluorphore absorbed energy is transferred to and absorbed by such absorber complex as is present in said reaction mixture, and wherein another portion of said fluorophore absorbed energy is emitted by said fluorophore as light of the second wavelength; and detecting said light of the second wavelength emitted by said fluorophore of said reaction mixture, said detected emitted light being a measure of the analyte of interest in the sample.

3. A method for detecting an analyte of interest in a fluid sample, said method comprising the steps of:

mixing the fluid sample comprising a discrete ligand whose presence is indicative of the analyte of interest in the sample with a specifically binding proto-absorber whose spectral properties are influenced by and correlatable with said ligand and which has a definable light absorption spectrum in the unbound state, at least a portion of said proto-absorber binding with such ligand as is present to form a complex while the remainder of said proto-absorber remains unbound;

admixing a chemically non-reactive fluorophore with said unbound proto-absorber to form a reaction mixture, said fluorophore having a definable light absorption spectrum and a definable light emission spectrum each of which overlaps the light absorption spectrum of said unbound proto-absorber, said fluorophore of said formed reaction mixture being able (a) to absorb exciting light energy of a first wavelength, (b) to transfer a part of said fluorophore absorbed energy to said unbound proto-absorber of said reaction mixture for absorption, said transfer being selected from the group consisting of radiative and non-radiative energy transfers, and (c) to emit the other part of said fluorophore absorbed energy as emitted light of a second wavelength;

introducing exciting light energy of the first wavelength to said reaction mixture sufficient to cause said fluorophore to absorb said exciting light energy, wherein a portion of said fluorophore absorbed energy is transferred to and absorbed by such unbound proto-absorber as is present in said reaction mixture, and wherein another portion of said fluorophore absorbed energy is emitted by said fluorophore as light of the second wavelength; and detecting said light of the second wavelength emitted by said fluorophore of said reaction mixture, said detected emitted light being a measure of the analyte of interst in the sample.

4. A method for detecting an analyte of interest in a fluid sample, said method comprising the steps of:

admixing the fluid sample comprising a discrete absorber ligand whose spectral properties are influenced by and correlatable with the analyte of interest in the sample with a plurality of different chemically non-reactive fluorophores to form a reaction mixture, said absorber ligand having a definable light absorption spectrum, each of said different fluorophores having a definable light absorption spectrum and a definable light emission spectrum wherein at least one of said different fluorophores has a definable light absorption spectrum which overlaps the light absorption spectrum of said absorber ligand and another of said different fluorophores has a definable light emission spectrum which overlaps the light absorption spectrum of said absorber ligand, and wherein (a) at least one fluorophore of said formed reaction mixture is able to absorb exciting light energy of a first wavelength and to transfer at least a part of said fluorophore absorbed energy to another fluoropbore for energy absorption, (b) at least one other fluorophore of said reaction mixture is able to absorb energy transferred from a different fluorophore and to emit at least part of said absorbed energy as emitted light of a second wavelength, and (c) at least one of said different fluorophores transfers at least a part of said fluorophore absorbed energy to said absorber ligand for absorption, said transfer being selected from the group consisting of radiative and non-radiative energy transfers;

introducing exciting light energy of the first wavelength to said reaction mixture sufficient to cause at least one of said different fluorophores to absorb said exciting light energy wherein portions of said fluorophore absorbed energy are transferred to and absorbed by at least one other of said fluorophores and such absorber ligand as is present in said reaction mixture, and wherein at least one other portion of said fluorophore absorbed energy is emitted by said fluorophore as light of the second wavelength; and detecting said light of the second wavelength emitted by said fluorophore of said reaction mixture, said detected emitted light being a measure of the analyte of interest in the sample.

5. A method for detecting an analyte of interest in a fluid sample, said method comprising the steps of:

mixing the fluid sample comprising a discrete ligand whose presence is indicative of the analyte of interest in the sample with a specifically binding proto-absorber whose spectral properties are influenced by and correlatable with said ligand to form an absorption complex having a definable light absorption spectrum, at least a portion of said proto-absorber binding with such ligand as is present to form said absorption complex while the remainder of said proto-absorber remains unbound;

admixing a plurality of different chemically non-reactive fluorophores with said absorption complex to form a reaction mixture, each of said fluorophores having a definable light absorption spectrum and a definable light emission spectrum wherein at least one of said different fluorophores has a definable light absorption spectrum which overlaps the light absorption spectrum of said absorption complex and another of said different fluorophores has a definable light emission spectrum which overlaps the light absorption spectrum of said absorption complex, and wherein (a) at least one fluorophore of said formed reaction mixture is able to absorb exciting light energy of a first wavelength and to transfer a part of said fluorophore absorbed energy to another fluorophore for energy absorption, (b) at least one other fluorophore is able to absorb energy transferred from a different fluorophore and to emit said absorbed energy as emitted light of a second wavelength, (c) at least one of said fluorophores transfers at least a part of said fluorophore absorbed energy to said absorption complex for energy absorption, said transfer being selected from the group consisting of radiative and non-radiative energy transfers;

introducing exciting light energy of the first wavelength to said reaction mixture sufficient to cause at least one of said different fluorophores to absorb said exciting light energy, wherein portions of said fluorophore absorbed energy are transferred to and absorbed by at least one other of said fluorophores and such absorber complex as is present in said reaction mixture, and wherein a portion of said fluorophore absorbed energy is emitted by a fluorophore as light of the second wavelength; and detecting said light of the second wavelength emitted by said fluorophore of said reaction mixture, said detected emitted light being a measure of the analyte of interest in the sample.

6. A method for detecting an analyte of interest in a fluid sample, said method comprising the steps of:

mixing the fluid sample comprising a discrete ligand whose presence is indicative of the analyte of interest in the sample with a specifically binding proto-absorber whose spectral properties are influenced by and correlatable with said ligand and which has a definable light absorption spectrum in the unbound state, at least a portion of said proto-absorber binding with such ligand as is present to form a complex while the remainder of said proto-absorber remains unbound;

admixing a plurality of different chemically non-reactive fluorophores with said unbound proto-absorber to form a reaction mixture, each of said fluorophores having a definable light absorption spectrum and a definable light emission spectrum wherein at least one of said different fluorophores has a definable light absorption spectrum which overlaps the light absorption spectrum of said unbound proto-absorber and another of said different fluorophores has a definable light emission spectrum which overlaps the light absorption spectrum of said unbound proto-absorber, and wherein (a) at least one fluorophore of said formed reaction mixture is able to absorb exciting light energy of a first wavelength and to transfer a part of said fluorophore absorbed energy to another fluorophore for energy absorption, (b) at least one other fluorophore is able to absorb energy transferred from a different fluorophore and to emit said absorbed energy as light of a second wavelength, (c) at least one of said fluorophores transfers at least a part of said fluorophore absorbed energy to said unbound proto-absorber for energy absorption, said transfer being selected from the group consisting of radiative and non-radiative energy transfers;

introducing exciting light energy of the first wavelength to said reaction mixture sufficient to cause at least one of said different fluorophore to absorb said exciting light energy, wherein portions of said fluorophore absorbed energy are transferred to and absorbed by at least one other of said fluorophores and such unbound proto-absorber as is present in said reaction mixture, and wherein a portion of said fluorophore absorbed energy is emitted by a fluorophore as light of the second wavelength; and detecting said light of the second wavlength emitted by said fluorophore of said reaction mixture, said detected emitted light being a measure of the analyte of interest in the sample.

7. The method as recited in claim 1, 2, 3, 4, 5, or 6 wherein said fluorophore is immobilized using a porous matrix.

8. The method as recited in claim 2, 3, 4, 5, or 6 wherein said proto-absorber is immobilized using a porous matrix.

9. The method as recited in claim 1, 2, 3, 4, 5, or 6 wherein said discrete ligand is a fluorescent material.

10. The method as recited in claim 1, 2, 3, 4, 5, or 6 wherein the analyte of interest and said discrete ligand are identical.

11. The method as recited in claim 1, 2, 3, 4, 5, or 6 wherein said introduction of exciting light is achieved using a fiber optic sensor.

12. The method as recited in claim 1, 2, 3, 4, 5, or 6 wherein said detection of emitted light from said admixture is achieved using a fiber optic sensor.

13. The method as recited in claim 1, 2, 3, 4, 5, or 6 wherein said fluorophore is selected from the group consisting of eosin, eosin derivatives, rhodamine, rhodamine derivatives, fluorescein, fluorescein derivatives, acridine, acridine derivatives, erhthroscein, and cyanosine.

14. The method as recited in claim 2, 3, 5, or 6 wherein said proto-absorber is selected from the group consisting of phenol red, brilliant yellow, rosolic acid, pararosaniline, ortho cresolphthalein, and bromo pyrogalol red.

* * * * *